US011371980B2

(12) United States Patent
Fujioka et al.

(10) Patent No.: US 11,371,980 B2
(45) Date of Patent: Jun. 28, 2022

(54) METHOD FOR TREATING BIOMOLECULES AND METHOD FOR ANALYZING BIOMOLECULES

(71) Applicant: HITACHI HIGH-TECH CORPORATION, Tokyo (JP)

(72) Inventors: Michiru Fujioka, Tokyo (JP); Yusuke Goto, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 117 days.

(21) Appl. No.: 16/340,995

(22) PCT Filed: Oct. 20, 2016

(86) PCT No.: PCT/JP2016/081092
§ 371 (c)(1),
(2) Date: Apr. 10, 2019

(87) PCT Pub. No.: WO2018/073934
PCT Pub. Date: Apr. 26, 2018

(65) Prior Publication Data
US 2020/0041483 A1 Feb. 6, 2020

(51) Int. Cl.
C12Q 1/6806 (2018.01)
G01N 33/487 (2006.01)
C12Q 1/6869 (2018.01)
G01N 27/447 (2006.01)
C12Q 1/6839 (2018.01)
C12Q 1/6832 (2018.01)

(52) U.S. Cl.
CPC ..... *G01N 33/48721* (2013.01); *C12Q 1/6806* (2013.01); *C12Q 1/6832* (2013.01); *C12Q 1/6839* (2013.01); *C12Q 1/6869* (2013.01); *G01N 27/4473* (2013.01); *G01N 27/44791* (2013.01)

(58) Field of Classification Search
None
See application file for complete search history.

(56) References Cited

U.S. PATENT DOCUMENTS

| | | | |
|---|---|---|---|
| 5,702,896 A | 12/1997 | Collins et al. | |
| 6,410,231 B1* | 6/2002 | Arnold | C12Q 1/6827 435/6.1 |
| 2002/0110900 A1* | 8/2002 | Jovanovich | C12Q 1/6869 435/288.1 |
| 2003/0082557 A1* | 5/2003 | Taylor | C12Q 2527/125 435/6.12 |
| 2005/0106589 A1 | 5/2005 | Akhavan-Tafti et al. | |
| 2007/0099295 A1 | 5/2007 | Maine et al. | |
| 2007/0264652 A1* | 11/2007 | Upadhyay | C12Q 1/6816 435/6.12 |
| 2008/0199872 A1* | 8/2008 | Barnard | C12Q 1/6855 435/6.14 |
| 2009/0048439 A1* | 2/2009 | Weisburg | C12N 15/1006 536/25.41 |
| 2010/0148126 A1 | 6/2010 | Guan et al. | |
| 2012/0193235 A1 | 8/2012 | Afzali-Ardakani et al. | |
| 2013/0220811 A1 | 8/2013 | Aksimentiev | |
| 2013/0327656 A1* | 12/2013 | Van Grinsven | C12Q 1/6827 205/780.5 |
| 2014/0158540 A1 | 6/2014 | Ohura | |
| 2017/0268054 A1 | 9/2017 | Akahori et al. | |
| 2018/0217123 A1 | 8/2018 | Goto et al. | |

FOREIGN PATENT DOCUMENTS

| | | |
|---|---|---|
| CN | 105372303 A | 3/2016 |
| JP | 2008-104424 A | 5/2008 |
| JP | 2009-515169 A | 4/2009 |
| JP | 2014-074599 A | 4/2014 |
| JP | 2016-057263 A | 4/2016 |
| JP | 2016-106563 A | 6/2016 |
| WO | 2013021815 A1 | 2/2013 |

OTHER PUBLICATIONS

Of Wang et al. (Y Wang, F Yao, X-F Kang, Tetramethylammonium-filled protein nanopore for single-molecule analysis, Anal. Chem., 87 (2015) 9991-9997) (Year: 2015).*
Blanco, Fernando et al.; Non-Covalent Interactions: Complexes of Guanidinium with DNA and RNA Nucleobases; J. Phys. Chem. B; 2013; 117; pp. 11608-11616.
Wang, Ying et al.; "Tetramethylammonium-Filled Protein Nanopore for Single-Molecule Analysis"; Anal. Chem., 2015, vol. 87, pp. 9991-9997.
Higuchi, Kobunshi, "Interaction Between Nucleic Acids and Ions"; The Society of Polymer Science, Japan; vol. 22; 1973; pp. 371-377.
Anderson, Brett N. et al.; pH Tuning of DNA Translocation Time Through Organically Functionalized Nanopores; Feb. 26, 2013; ACS Nano; pp. 1408-1414.
Kowalczyk, Stefan W et al.; "Slowing Down DNA Translocation Through a Nanopore in Lithium Chloride"; Nano Lett. 2012; vol. 12 pp. 1038-1044.
Winters-Hilt, Stephen et al.; "Nanopore-Based Kinetics Analysis of Individual Antiobody-Channel and Antibody-Antigen Interactions"; Nov. 2007; pp. 1-17.
International Search Report of PCT/JP2016/081092, dated Dec. 27, 2016.
Fologea, D. et al.; "Slowing DNA Translocation in a Solid-State Nanopore"; vol. 5; No. 9; pp. 1734-1737.
Akahori, R. et al.; "Slowing Single-Stranded DNA Translocation Through a Solid-State Nanopore by Decreasing the Nanopore Diameter"; 2014; 25; 275501; pp. 1-6.
Squires, A. H. et al.; "A Nanopore-Nanofiber Mesh Biosensor to Control DNA Translocation"; 2013; pp. 16304-16307.

(Continued)

*Primary Examiner* — Robert T. Crow
(74) *Attorney, Agent, or Firm* — Miles & Stockbridge P.C.

(57) ABSTRACT

The purpose of the present invention is to provide a method for treating biomolecules and a method for analyzing biomolecules with which it is possible to effectively suppress the clog of nanopores. The present invention is a method for treating biomolecules for analysis in which nanopores are used, wherein the method includes a step for preparing a sample solution that includes ammonium cations represented by a prescribed formula and biomolecules in which at least a portion of the higher-order structure has been fused.

8 Claims, 2 Drawing Sheets

(56) References Cited

OTHER PUBLICATIONS

Wanunu, M. et al.; "Electrostatic Focusing of Unlabelled DNA into Nanoscale Pores Using a Salt Gradient"; vol. 5 2010; pp. 160-165.
Rincon-Restrepo, M. et al.; "Controlled Translocation of Individual DNA Molecules Through Protein Nanopores with Engineered Molecular Brakes"; 2011; pp. 746-750.
Sun et al.; "ZQ Sun, X Chen, JH Zhang, ZM Chen, K Zhang, X Yan, YF Wang, WZ Yu, B Yang, "Nonspherical Colloidal Crystals Fabricated by the Thermal Pressing of Colloidal Crystal Chips, Langmuir 21; (2005); 8987-8991) (Year 2005).
Chen et al. (Z Chen, Y Jiang, DR Dunphy, DP Adams, C Hodges, N Liu, N Zhang, G Xomeritakis, X Jin, NR Aluru, SJ Gaik, HW Hillhouse, CJ Brinker, DNA translocation through an array of kinked nanopores, Nature Materials, 9 (2010) 667-675). (Year: 2010).
Kosiorek et al. (A Kosiorek, W Kandulski, H Glaczynska, M Giersig, Fabrication of nanoscale rings, dots, and rods by combining shadow nanosphere lithography and annealed polystyrene nanosphere masks, Small 1 (4) (2005) 439-444). (Year: 2005).
Venta et al. (K Venta, G Shemer, M Puster, JA Rodriguez-Manzo, A Balan, JK Rosenstein, K Shepard, M Dmdic, Differentiation of short, single-stranded DNA homopolymers in solid-state nanopores, ACS Nano, 7(5) (2013) 4629-4636). (Year: 2013).
Reina et al. (JP2014074599 A, Machine Translation) (Year: 2014).
Vandeventer et al.; Multiphasic DNA Adsorption to Silica Surfaces under Varying Buffer, pH and Ionic Strength Conditions, J. Phys. Chern. B, 116 (2012) 5661-5670). (Year 2012).
Office Action dated Nov. 30, 2021 in Chinese Application No. 201680090131.

\* cited by examiner

[Fig. 1]
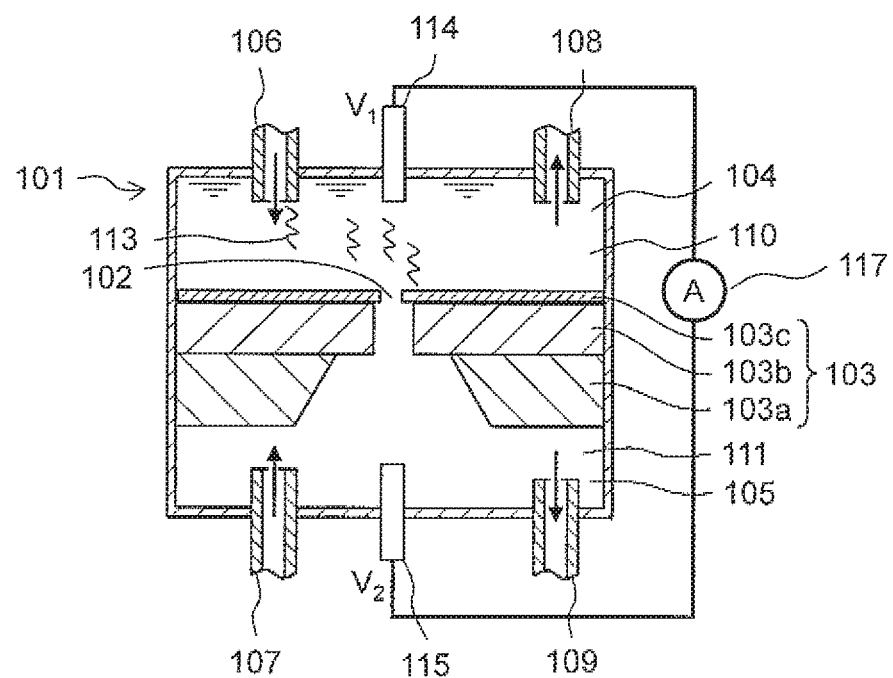

[Fig. 2]
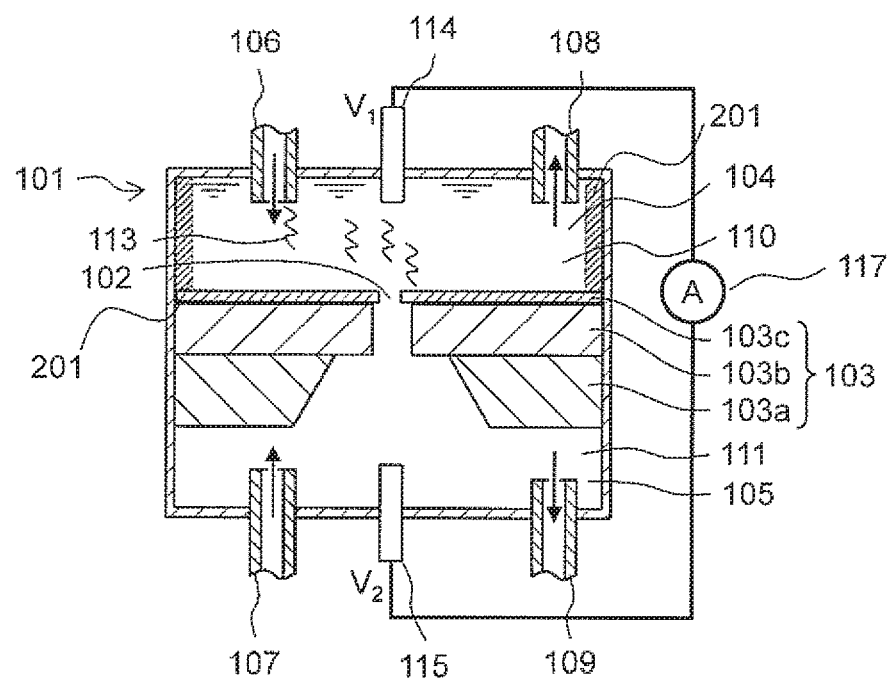

METHOD FOR TREATING BIOMOLECULES AND METHOD FOR ANALYZING BIOMOLECULES

TECHNICAL FIELD

The present invention relates to a method for treating a biomolecule and a method for analyzing a biomolecule.

BACKGROUND ART

Techniques of assaying base sequences of nucleic acid which is one of biomolecules are very important because of applicability to detection of a gene responsible for an inherited disease, evaluation of effectiveness and side effects of a drug, detection of a gene mutation associated with a cancer disease, and the like. A base sequence of a nucleic acid can be assayed using a fluorescent detection instrument (3500 Genetic Analyzer manufactured by Thermo Fisher Scientific) by electrophoresis with a capillary, an instrument for detecting a nucleic acid immobilized on a plate by fluorescence (HiSeq 2500 manufactured by illumina, Inc.), or the like. However, since such instruments require expensive fluorescent detectors and fluorescent regents, the cost for testing tends to be high.

Thus, as an assay technique for low cost detection, a method of assaying a base sequence of a nucleic acid by detecting variation in optical signal or electrical signal generated when the nucleic acid is passing through a nanopore has been studied. First, a hole of several nanometers (nanopore) is formed in a thin film of 1 to 60 nm using a transmission electron microscope. Next, a liquid chamber filled with an electrolytic solution is provided on each side of the thin film, and an electrode is provided in each of the liquid chambers. When a voltage is applied between the electrodes, an ionic current flows through the nanopore. The ionic current is proportional to the sectional area of the nanopore. When a DNA passes through the nanopore, the DNA clogs the nanopore to reduce the effective sectional area of the nanopore, leading to decrease of the ionic current. The ionic current varied by the passing of the DNA is referred to as a blockage current. Difference between a single strand and a double strand of a DNA and the types of bases can be determined on the basis of the magnitude of the blockage current. In determination of the types of bases, since the current value differs depending on the type of base, a highly conductive measurement sample solution, which shows low noise and in which a larger current flows, is preferred from the viewpoint of accurate determination of each base.

The subject of the analytical technique using a nanopore is not limited to a DNA, and examples of subjects include biomolecules, such as an RNA, a peptide, and a protein. A DNA, which is negatively charged, passes through a nanopore from the negative electrode side to the positive electrode side.

Known examples of bases contained in DNA, which is one of biomolecules, include adenine and guanine which have a purine skeleton and cytosine and thymine (uracil in RNA) which have pyrimidine skeleton. Each combination of adenine and thymine, and cytosine and guanine, are known to form a hydrogen bond, and a double helix structure of DNA is formed owing to the hydrogen bond and the like, causing self-hybridization which leads to formation of a higher-order structure of a single strand DNA. The double helix structure of DNA and a higher-order structure of single strand DNA have a larger 3D-structure than a nanopore, and thus largely interfere with passing of a DNA through a nanopore. Due to the structure, a nanopore may be clogged. When the nanopore is clogged, passing of the DNA after the clog is inhibited.

Against the problem regarding the clog, PTL 1 discloses a technique for eliminating clog of a nanopore by irradiating the nanopore with a laser beam as a heat source.

With respect to the nanopore technology, NPL 1 reports results of measuring blockage currents in a protein pore using a sample solution for blockage current measurement containing tetramethylammonium chloride. NPL 1 describes an effect of increasing stability of lipid bilayers by tetramethylammonium chloride in the case of a protein pore.

CITATION LIST

Patent Literature

PTL 1: US Patent Application Publication No. 2013/0220811

Non-Patent Literature

NPL 1: Ying Wang, et. al., "Tetramethylammonium-Filled Protein Nanopore for Single-Molecule Analysis", Anal. Chem. 2015, 87, 9991-9997)

SUMMARY OF INVENTION

Technical Problem

As described above, in techniques of analyzing a biomolecule, such as a nucleic acid, using a nanopore, the biomolecule may clogs the nanopore. Against the problem, PTL 1 proposes a technique for eliminating the clog by laser irradiation. However, a laser installation leads to an expensive analyzer having a complex configuration. In addition, the Brownian motion of a biomolecule may become larger due to the heat generated by laser irradiation. When the Brownian motion of a biomolecule becomes larger, the motion of the biomolecule passing through the nanopore becomes larger, and thus the blockage current value may be unstable. Accordingly, accurate analysis of the biomolecule may be difficult.

NPL 1 reports that current measurement of a DNA sometimes cannot be performed due to self-hybridization depending on the sequence. Since DNA has a variety of sequences, it is desired that an assay can be performed even for a DNA having a sequence that is liable to form a higher-order structure. PTL 2 (JP-A-2008-104424) reports that the tetramethylammonium cation, which is used in NPL 1, suppresses nonspecific hybridization in the hybridization reaction of a DNA, leading to efficient formation of only specific hybridization. This shows that a nanopore may be clogged by self-hybridization, making a current measurement difficult even with a tetramethylammonium cation.

Thus, an object of the present invention is to provide a method for treating a biomolecule and a method for analyzing a biomolecule with which clog of a nanopore can be effectively suppressed.

Solution to Problem

Modes of the present invention is as follows.

(1) A method for treating a biomolecule for an analysis using a nanopore, the method including a step of providing a sample solution, the sample solution containing an ammonium cation represented by a formula (1)

shown below and a biomolecule with at least a part of a higher-order structure fused:

[Chem. 1]

Formula (1)

wherein $R_1$ to $R_4$ each independently represent a hydrogen atom or an organic group, provided that not all of $R_1$ to $R_4$ are hydrogen atoms.
(2) The method according to (1), wherein the cation is a quarternary ammonium cation.
(3) The method according to (1) or (2), wherein the cation is a quarternary alkyl ammonium cation.
(4) The method according to any one of (1) to (3), wherein the step of providing the sample solution includes steps of: mixing at least the cation and the biomolecule to prepare a solution; and subjecting the solution to a heat treatment to fuse the at least a part of the higher-order structure of the biomolecule.
(5) The method according to (4), which includes a step of subjecting the solution after the fusing step to a cooling treatment.
(6) The method according to any one of (1) to (3), wherein the step of providing the sample solution includes a step of mixing at least the cation, the biomolecule, and a pH adjuster for adjusting the pH of the sample solution to a pH at which the higher-order structure of the biomolecule is fused.
(7) The method according to any one of (1) to (3), wherein the step of providing the sample solution includes a step of mixing at least the cation, the biomolecule, and a denaturant for fusing the higher-order structure of the biomolecule.
(8) The method according to any one of (1) to (7), wherein the sample solution further includes an electrolyte that has a higher electrical conductivity than a salt used for incorporating the cation into the sample solution.
(9) The method according to (8), wherein the cation is a quarternary ammonium cation and the electrolyte is an ammonium salt.
(10) The method according to any one of (1) to (9), wherein the biomolecule is a nucleic acid.
(11) A method for analyzing a biomolecule using an instrument provided with a substrate having a nanopore, the method including steps of:
    treating the biomolecule by the method according to any one of (1) to (10) to provide a sample solution; and
    detecting an optical signal or an electrical signal when the biomolecule in the sample solution is passing through the nanopore.
(12) A method for analyzing a biomolecule using an instrument, the instrument being provided with a substrate having a nanopore and a sample introducing area, the method including steps of:
    preparing a solution that contains an ammonium cation represented by the formula (1) and the biomolecule;
    placing the solution in the sample introducing area;
    subjecting the solution in the sample introducing area to a heat treatment to fuse at least a part of a higher-order structure of the biological sample; and
    detecting an optical signal or an electrical signal when the biomolecule is passing through the nanopore after the fusing step.
(13) The method according to (11) or (12), which further includes a step of performing, in the case where the nanopore is clogged, a heat treatment to eliminate the clog.
(14) The method according to any one of (11) to (13), wherein the substrate is a solid substrate.

Advantageous Effects of Invention

The present invention can provide a method for treating a biomolecule and a method for analyzing a biomolecule with which clog of a nanopore can be effectively suppressed.

BRIEF DESCRIPTION OF DRAWINGS

FIG. 1 It is a schematic sectional view for explaining a configuration of a chamber unit of a nanopore analyzer provided with a substrate having a nanopore.
FIG. 2 It is a schematic sectional view for explaining a configuration of a chamber unit of a nanopore analyzer provided with a substrate having a nanopore and a temperature controlling means.

DESCRIPTION OF EMBODIMENTS

As used herein, the term "biomolecule" refers to a biopolymer present in organisms, such as a nucleic acid (for example, DNA or RNA), a peptide, a polypeptide, a protein, or a carbohydrate chain. The nucleic acids include a single strand, double strand, or triple strand DNAs and RNAs, and any chemical modified forms thereof.
As used herein, the term "analysis" means determination, detection, and identification of the characteristics of a biomolecule, for example, determination of a sequence of a component of the biomolecule. As used herein, sequencing of a biomolecule refers to determination of a sequence of a component (base) of a biomolecule (for example, a DNA or RNA).
As used herein, the term "nanopore" refers to a hole having a nano-order size (specifically, a diameter of 0.5 nm or more and less than 1 m). A nanopore is provided through the substrate, and is communicated with a sample introducing area and a sample flow-out area.
Embodiments of the present invention will be described below.
One embodiment of the present invention is a method for treating a biomolecule for an analysis using a nanopore, the method including a step of providing a sample solution containing an ammonium cation represented by the formula (1) and a biomolecule with at least a part of a higher-order structure fused.
The analysis using a nanopore specifically refers to an analysis of a biomolecule by detecting an optical signal or an electrical signal when the biomolecule is passing through a nanopore using a substrate having the nanopore (hereinafter also referred to as nanopore substrate), and, for example, refers to an analysis of a base sequence of a nucleic acid using a nucleic acid sequencer provided with a nanopore substrate.
In this embodiment, the sample solution contains at least an ammonium cation represented by the formula (1) (hereinafter also referred to as cation (A)) and a biomolecule with at least a part of a higher-order structure fused.
The cation (A) can approach the biomolecule by electrostatic interaction and thus can prevent the biomolecule with a higher-order structure fused from forming a higher-order structure again.

As the cation (A), one ion species may be used alone or two or more species may be used in combination. The cation (A) can be incorporated into a sample solution, for example, using a salt containing the cation (A). Examples of salts containing the cation (A) include, but not limited to, chlorides and hydroxides.

In the formula (1), the carbon number of the organic group is preferably 1 to 4, more preferably 1 to 3, and further preferably 1 to 2. The organic group is preferably a hydrocarbon group. The carbon number of the hydrocarbon group is preferably 1 to 4, more preferably 1 to 3, and further preferably 1 to 2. The hydrocarbon group may have a substituent. The hydrocarbon group is preferably an alkyl group, an alkenyl group, or an alkynyl group, and more preferably an alkyl group.

The ammonium cation (A) is preferably a quarternary ammonium cation. Specifically, in the formula (1), $R_1$ to $R_4$ preferably each independently represent an organic group.

The ammonium cation (A) is more preferably a quarternary alkyl ammonium cation. Specifically, in the formula (1), $R_1$ to $R_4$ preferably each independently represent an alkyl group. The alkyl group may have a linear, branched, or cyclic shape. The alkyl group preferably has a linear shape or a branched shape, and more preferably a linear shape. The carbon number of the alkyl group is preferably 1 to 4, more preferably 1 to 3, and further preferably 1 to 2.

Examples of quarternary alkyl ammonium cations include a tetramethylammonium cation (hereinafter also referred to as TMA+), a tetraethylammonium cation (hereinafter also referred to as TEA+), and a tetrapropyl ammonium cation (hereinafter also referred to as TPA+). Examples of salts of quarternary alkyl ammonium cations include chlorides and hydroxides as described above. Specific examples include tetramethylammonium chloride, tetraethylammonium chloride, tetrapropylammonium chloride, tetramethylammonium hydroxide, tetraethylammonium hydroxide, and tetrapropylammonium hydroxide.

The concentration of the cation (A) in the sample solution is for example, but not limited to, 0.1 to 4.0 M, and preferably 0.5 to 3.0 M.

The pH of the sample solution is preferably 7.5 or higher, more preferably 8.0 or higher, and further preferably 8.6 or higher. With a pH of 7.5 or higher, the clog of a nanopore can be further effectively suppressed. The pH of the sample solution is preferably 11.0 or lower, and more preferably 10.0 or lower. With a pH of 11.0 or lower, damage to a nanopore substrate can be reduced.

The sample solution can contain an ion other than the cation (A). For example, the sample solution can contain an electrolyte. The electrolyte preferably has a higher electrical conductivity than the salt containing the cation (A) which is used for incorporating the cation (A) into the sample solution. As an electrolyte having such a high electrical conductivity (also referred to as highly conductive electrolyte), for example, ammonium chloride, potassium chloride, sodium chloride, or cesium chloride may be mentioned. Other examples include salts of primary amines, salts of secondary amines, and salts of guanidine compounds. In particular, when the cation (A) is a quarternary ammonium cation (for example, a quarternary alkyl ammonium cation), from the viewpoint of electrical conductivity and reduction of noise, the highly conductive electrolyte is preferably a salt containing an ammonium ion, and more preferably ammonium chloride or ammonium hydroxide. The concentration of the electrolyte is preferably 0.1 to 3.0 M, more preferably 0.5 to 2.5 M, and further preferably 1.0 to 2.0 M. The electrical conductivity of the quarternary alkyl ammonium salt is lower than the electrical conductivity of commonly used electrolytes, such as potassium chloride. For this reason, when a biomolecule (for example, nucleic acid) is subjected to an analysis (for example, a base sequence analysis) by the blockage current, an electrolyte having a higher electrical conductivity is preferably further added to a sample solution in addition to a salt containing the cation (A) from the viewpoint of the accuracy. With an increased amount of the highly conductive electrolyte, the electrical conductivity of the sample solution tends to increase to reduce the noise.

However, excessive cations other than the cation (A) in the sample solution lead to possibility of inhibiting the clog suppression effect of the cation (A). Thus, the ratio (by mole) of the salt containing the cation (A) and the highly conductive electrolyte is preferably 4:1 to 1:4, and more preferably 2:1 to 1:2.

The electrical conductivity [mS/cm] of a compound can be measured herein using an aqueous solution (25° C.) containing the target compound at 1 M.

The sample solution can contain a solvent, such as water, a pH adjuster, a denaturant, or other additives. As the pH adjuster, for example, a buffer is mentioned. The buffer can be appropriately selected according to the characteristics of the biomolecule, and examples include Tris or Tris-HCl, carbonate-bicarbonate buffer, sodium borate buffer, and phosphate buffer. Among them, Tris or Tris-HCL is preferred since the pH of the sample solution is easily controlled in the range of 7.5 or higher.

As used herein, "a higher-order structure is fused" means that the higher-order structure is released, and, for example, that a self-hybridization structure of a single strand nucleic acid or a hybridization structure of a double strand nucleic acid or a triple strand nucleic acid is released, or a higher-order structure of a protein is released.

The biomolecule with at least a part of a higher-order structure fused is obtained, for example, by a heat treatment, a pH adjustment with a pH adjuster, or use of a denaturant.

In one suitable embodiment, the step of providing the sample solution includes steps of: mixing at least the cation (A) and a biomolecule to prepare a solution; and subjecting the solution to a heat treatment to fuse at least a part of a higher-order structure of the biomolecule. That is, in the embodiment, a solution that contains the cation (A) and the biomolecule is first prepared. Then, the solution is subjected to a heat treatment to provide a sample solution. In the embodiment, the biomolecule with at least a part of a higher-order structure fused can be obtained by a heat treatment. In this embodiment, the biomolecule is preferably a nucleic acid. The temperature of the heat treatment is preferably 60 to 100° C., and more preferably 90 to 100° C. A cooling treatment may be performed after the heat treatment, and in the cooling treatment, the solution after the heat treatment is preferably rapidly cooled. By the cooling treatment, reformation of a higher-order structure can be effectively suppressed. A rapid cooling treatment is a treatment for decreasing a temperature, for example, at 1° C./s or more (preferably 5° C./s or more, more preferably 10° C./s or more, and particularly preferably 20° C./s or more). The temperature after cooling is preferably 0 to 10° C., and more preferably 0 to 4° C.

In one suitable embodiment, the step of providing a sample solution includes a step of mixing at least the cation (A), a biomolecule, and a pH adjuster for adjusting the pH of the sample solution to a pH at which a higher-order structure of the biomolecule is fused. That is, in the embodiment, a solution containing at least the cation (A), a biomolecule, and a pH adjuster for adjusting the pH of the sample solution to a pH at which a higher-order structure of the biomolecule is fused is prepared to thereby provide a sample solution. In the embodiment, the biomolecule with at least a part of a higher-order structure fused is obtained by the action of a pH adjuster. As the pH adjuster, for example, a buffer can be used. In this embodiment, from the viewpoint of fusing a higher-order structure (for example, a higher-order structure of a nucleic acid), the pH value is preferably 9.0 or higher, and more preferably 10.0 or higher. From the viewpoint of stability of the nanopore substrate, the pH is preferably 11.0 or lower.

In one suitable embodiment, the step of providing a sample solution includes a step of mixing at least the cation (A), a biomolecule, and a denaturant for fusing a higher-order structure of the biomolecule. That is, in the embodiment, a solution containing at least the cation (A), a biomolecule, and a denaturant for fusing a higher-order structure of the biomolecule is prepared to thereby provide a sample solution. The biomolecule with at least a part of a higher-order structure fused is obtained by an action of denaturation based on the denaturant. Examples of denaturants that can be used include, but not limited to, formamide, formaldehyde, urea, and DMSO in the case where the biomolecule is a nucleic acid, and examples thereof include urea and guanidine in the case where the biomolecule is a protein. The concentration of the denaturant is not limited, but is preferably appropriately selected according to the biomolecule.

One embodiment of the present invention is a method for analyzing a biomolecule using an instrument provided with a substrate having a nanopore (hereinafter referred to as a nanopore-type analyzer), the method including steps of: treating a biomolecule by a treatment method according to the embodiment to provide a sample solution; and detecting an optical signal or an electrical signal when the biomolecule in the sample solution is passing through the nanopore.

The sample solution can be provided before being introduced into a nanopore-type analyzer, such as a nanopore sequencer. After the solution containing the cation (A) and a biomolecule is introduced into the nanopore-type analyzer, the fusing step, such as a heat treatment, may be performed to provide a sample solution (specifically, containing the cation (A) and a biomolecule with at least a part of a higher-order structure fused). That is, a sample solution can be provided by placing a solution containing the cation (A) and a biomolecule in a sample introducing area of a nanopore instrument and then performing a heat treatment by a temperature controlling means provided in the nanopore-type analyzer.

That is, one suitable embodiment of the present invention is a method for analyzing a biomolecule using an instrument, the instrument being provided with a substrate having a nanopore and a sample introducing area, the method including steps of: preparing a solution that contains the cation (A) and the biomolecule; placing the solution in the sample introducing area; subjecting the solution in the sample introducing area to a heat treatment to fuse at least a part of a higher-order structure of the biomolecule; and after the fusing step, detecting an optical signal or an electrical signal when the biomolecule is passing through the nanopore.

FIG. 1 shows a schematic sectional view for explaining a configuration example of a chamber unit of a nanopore-type analyzer that can be used for an analytical method according to this embodiment. In FIG. 1, a chamber unit 101 includes a sample introducing area 104, a sample flow-out area 105, a substrate (nanopore substrate) 103 having a nanopore 102 disposed between the sample introducing area 104 and the sample flow-out area 105. The sample introducing area 104 and the sample flow-out area 105 are spatially communicated with each other via the nanopore 102, and a biomolecule as a sample 113 can move from the sample introducing area 104 to the sample flow-out area 105 through the nanopore 102. A first liquid 110 is filled in the sample introducing area 104 via a first flow-in channel 106. A second liquid 111 is filled in the sample flow-out area 105 via a second flow-in channel 107. The first liquid 110 and the second liquid 111 can flow out of the sample introducing area 104 and the sample flow-out area 105 via a first flow-out channel 108 and a second flow-out channel 109, respectively. In analysis, the first liquid 110 and the second liquid 111 each may flow or may not flow from the flow-in channel to the flow-out channel. The first flow-in channel 106 and the second flow-in channel 107 may be provided at opposite positions across the substrate. In the same manner, the first flow-out channel 108 and the second flow-out channel 109 may be provided at opposite positions across the substrate.

In this embodiment, the substrate 103 includes a base (base material) 103a and a thin film 103b formed on the base 103a. The substrate 103 may include an insulating layer 103c formed on the thin layer 103b. The nanopore is formed in the thin layer 103b. By forming a thin layer on the base 103a with a material and thickness suitable for forming a nanopore, a nanopore can be provided in the substrate in an easy and efficient manner. The substrate is preferably a solid substrate. Examples of materials forming the thin layer include solid films of graphene, silicon, silicon compounds (for example, silicon oxide, silicon nitride, silicon oxynitride), metal oxides, and metal silicates. In one preferred embodiment, the thin layer is formed of a material containing silicon or a silicon compound. The thin layer (and the whole substrate in some cases) may be substantially transparent. "Substantially transparent", as used herein, means being capable of transmitting 50% or more, preferably 80% or more of external light. The thin layer may be a single layer or plural layers. The thickness of the thin layer is preferably 0.1 nm to 200 nm, preferably 0.1 nm to 50 nm, and more preferably 0.1 nm to 20 nm. The thin layer can be formed by any technique known in the art, for example, by a low pressure chemical vapor deposition (LPCVD).

In this embodiment, at least the first liquid 110 is the sample solution as described above. That is, the first liquid 110 is a sample solution containing a biomolecule as the sample 113 and the cation (A), and a higher-order structure of the biomolecule is in a fused state. The second liquid 111 may also contain the biomolecule and the cation (A). In this embodiment, the first liquid 110 may contain, in addition to the biomolecule and the cation (A), a solvent (preferably water) and an electrolyte (for example, ammonium chloride, KCl, or NaCl). The ions originated in the electrolyte can act as charge carriers.

The chamber unit 101 is provided with a first electrode 114 and a second electrode 115 disposed in the sample introducing area 104 and the sample flow-out area 105 oppositely across the nanopore 102. In this embodiment, the chamber unit is also provided with a means for applying a voltage to the first electrode 114 and the second electrode 115. By applying a voltage, the sample 113 bearing an electric charge moves from the sample introducing area 104 to the sample flow-out are 105 through the nanopore 102.

The nanopore-type analyzer may include, in addition to the chamber unit, a detection unit for detecting an optical signal or an electrical signal when the biomolecule is passing through the nanopore. The detection unit may include an amplifier that amplifies electrical signals, an A/D converter that converts an analog output of the amplifier to a digital output, a recorder for recording measured data, and the like.

The method for detecting an optical signal or an electrical signal when the biomolecule is passing through the nanopore is not limited, and, for example, a known detection method can be adopted. Specific examples of detection methods include a blockage current method, a tunnel current method, and a capacitance method. As one example, a detection method using a blockage current will be briefly described below. When a biomolecule (for example, a nucleic acid) passes through a nanopore, the biomolecule clogs the nanopore to thus reduce the ionic flow through the nanopore, resulting in reduction in the current (blockage current). The length and the base sequence of the individual nucleic acid molecule passing through the nanopore can be assayed by measuring the magnitude and the duration time of the blockage current. For example, regarding a tunnel current method, a biomolecule passing between the electrodes disposed in the vicinity of the nanopore can be detected by the tunnel current.

An example of methods of detecting variation of optical signal is a detection method using Raman light. For example, the biomolecule entering the nanopore is irradiated with external light (excitation light) to excite the biomolecule, generating Raman scattered light, and the characteristics of the biomolecule can be determined based on the spectrum of the Raman scattered light. In this case, the measurement unit may include a light source for emitting the external light and a detector (spectroscopic detector, or the like) for detecting Raman scattered light. A conductive thin layer may be placed in the vicinity of the nanopore to generate a near field to amplify the light. By using the detection by Raman light in addition to the detection by a blockage current method, a tunnel current method, or a capacitance method, the analytical accuracy can be increased.

The substrate 103 has at least one nanopore. The substrate 103 can be formed of an electrical insulating material, for example, an inorganic material and an organic material (including a polymer material). Examples of electrical insulating materials constituting the substrate include silicon, silicon compounds, glass, quart, polydimethylsiloxane (PDMS), polytetrafluoroethylene (PTFE), polystyrene, and polypropylene. Examples of silicon compounds include silicon nitride, silicon oxide, silicon carbide, and silicon oxynitride. In particular, a base (base material) constituting a supporting portion of the substrate can be made of any one of such materials, but preferably formed of, for example, a material containing silicon or a silicon compound (silicon material). Examples of materials constituting the thin layer in which the nanopore is formed include graphene, silicon, silicon compounds (for example, silicon oxide, silicon nitride, silicon oxynitride), metal oxides, and metal silicate salts as described above. Among them, a material containing silicon or a silicon compound is preferred. That is, in this embodiment, the nanopore is preferably formed in a member formed of a material containing silicon or a silicon compound.

The insulating layer 103c is preferably provided on the thin layer 103b. The thickness of the insulating layer is preferably 5 nm to 50 nm. Any insulating material can be used as a material of the insulating layer, but preferably, for example, a material containing silicon or a silicon compound (for example, silicon oxide, silicon nitride, silicon oxynitride) is used.

The substrate can be produced by any method known in the art. Alternatively, the substrate can be given as a commercial product. The substrate can be produced using a technique, such as photolithography, electron beam lithography, an etching method, a laser abrasion method, an injection molding method, a casting method, a molecular beam epitaxy, a chemical vapor deposition (CVD) method, a dielectric breakdown method, or an electron beam or focused ion beam method.

As the size of the nanopore, an appropriate size can be selected depending on the type of the biopolymer to be analyzed. The nanopore may have a uniform diameter or may have different diameters at different portions (for example, an ellipse shape). The nanopore can be joined with a pore having a diameter of 1 µm or more. The diameter of the nanopore is preferably 100 nm or less, preferably 0.5 nm to 100 nm, preferably 0.5 nm to 50 nm, and preferably 0.5 nm to 10 nm.

One example of the biomolecule to be analyzed is an ssDNA (single strand DNA). The maximum diameter of the ssDNA is about 1.5 nm, and an appropriate range of the nanopore diameter for analyzing an ssDNA is 1.5 nm to 10 nm, and preferably 1.5 nm to 2.5 nm. The diameter of a dsDNA (double strand DNA) is about 2.6 nm, and an appropriate range of the nanopore diameter for analyzing a dsDNA is 3 nm to 10 nm, and preferably 3 nm to 5 nm. Also in the case where another biomolecule, such as a protein, a polypeptide, or a carbohydrate chain is to be analyzed, the diameter of the nanopore can be selected in view of the size of the biomolecule.

The depth (length) of the nanopore can be adjusted by the thickness of a member in which the nanopore is formed (for example, the thickness of the thin layer 103b). The depth of the nanopore preferably corresponds to the monomer unit constituting the biomolecule to be analyzed. For example, when a nucleic acid is selected as the biomolecule, the depth of the nanopore is preferably a size of one base or less, for example, about 0.3 nm or less. The shape of the nanopore is basically a circular shape, but may be an elliptic or a polygonal shape.

At least one nanopore may be formed in the substrate. When plural nanopores are formed, the nanopores may be regularly arranged. The nanopore may be formed by any method known in the art, for example, by irradiation with an electron beam from a transmission electron microscope (TEM), or by use of a nanolithography technique or an ion beam lithography technique. The nanopore may also be formed in the substrate by electrical breakdown.

As described above, the chamber unit 101 can include, in addition to the sample introducing area 104, the sample flow-out area 105, and the substrate 103, the first electrode 114 and the second electrode 115 for causing the sample 113 to pass through the nanopore 102. In a suitable example, the chamber unit 101 includes the first electrode 114 provided in the sample introducing area 104, the second electrode 115 provided in the sample flow-out area 105, and a voltage applying means for applying a voltage to the first electrode and the second electrode. An ammeter 117 may be placed between the first electrode 114 provided in the sample introducing area 104 and the second electrode 115 provided in the sample flow-out area 105. The velocity of the sample passing through the nanopore can be adjusted by the current between the first electrode 114 and the second electrode 115. The current value can be appropriately selected by a person skilled in the art, but is preferably 100 mV to 300 mV in the case where the sample is a DNA.

A metal can be used as a material of the electrodes, and for example, a platinum group metal, such as platinum, palladium, rhodium, or ruthenium, gold, silver, copper, aluminum, nickel, graphite (single layer or multilayer), for example, graphene, tungsten, or tantalum may be mentioned.

FIG. 2 shows a configuration example of a chamber unit of a nanopore-type analyzer provided with a substrate having a nanopore and a temperature controlling means 201. The temperature controlling means 201 that can heat or cool the first liquid 110 in the sample introducing area 104 or the second liquid 111 in the sample flow-out area 105 can be provided. By the nanopore-type analyzer having a temperature controlling means 201 for controlling the temperature of the sample introducing area 104 or the sample flow-out area 105, a fusing treatment of a biomolecule can be performed in the instrument. When clog occurs in measurement, the clog can be eliminated by a heat treatment (and a cooling treatment, as needed) with the temperature controlling means 201.

EXAMPLES

Examples of the present invention will be described below.

(Preparation of Sample)

As a sample, a DNA having a length of several kilobases to several tens of kilobases was prepared by the following method. First, a sequence $A_{50}T_{25}C_{25}$ (single strand DNA) having 50 continuous adenine bases, 25 continuous thymine bases, and 25 continuous cytosine bases in this order was synthesized. The synthesized single strand DNA was cyclized using a single strand DNA ligase (CircLigase (trade name) ssDNA Ligase, manufactured by AR BROWN CO., LTD.), and was amplified using a phi29 DNA Polymerase (manufactured by New England BioLabs) to prepare a long chain (several kilobases to several tens of kilobases) DNA. Since the amplified DNA has a sequence having continuous adenine bases and thymine bases, the DNA relatively easily forms a higher-order structure by self-hybridization. Accordingly, the DNA can be suitably used for evaluation of the present invention. In the Examples, each of the sample solutions was provided so as to contain such a single strand DNA as described above as a sample at a concentration of 1.73 ng/µl.

Example 1

An aqueous solution having a composition 1 described below was subjected to a heat treatment and a cooling treatment to thereby provide a sample solution 1. As the heat treatment and cooling treatment, the aqueous solution was kept at 95° C. for 15 minutes, then was rapidly cooled to 4° C. (temperature decrease rate: 10° C./sec), and was kept at 4° C. for 5 minutes. Composition 1: 4.0 M tetramethylammonium chloride, 0.1 M Tris The sample solution was placed in the sample introducing area 104 of a nanopore-type analyzer having a configuration shown in FIG. 1, and the blockage current generated when the DNA was passing through the nanopore 102 was measured. The nanopore diameter was 1.1 to 1.8 nm. The blockage current was detected using a patch clamp amplifier (Axopatch 200B amplifiers, manufactured by Molecular instruments). The blockage current was detected under conditions of a sampling rate of 50 kHz and an applied voltage of +300 mV. The "clog", "number of events", "number of long term blockages", and "frequency" were evaluated based on the obtained detection data. The "number of events" shows the number of the events where the single strand DNA was considered to pass through the nanopore on the ground of reduction of the blockage current. The "number of long term blockages" shows the number of the cases where a state with the current value reduced was kept for 5 seconds or longer. The "frequency" was calculated by the formula: "number of long term blockages"/"number of events"×100(%). When a state with the current value reduced was kept for 5 seconds or longer, the blockage state of the nanopore by the DNA was eliminated by inverting the voltage to −300 mV. In the case where the blockage state of the nanopore was not eliminated by inverting the voltage, the "clog" was determined as "present".

Example 2

An aqueous solution having a composition 2 described below was subjected to the same heat treatment and cooling treatment as described in Example 1 to thereby provide a sample solution 2. Then, the blockage current was measured and evaluated in the same manner as in Example 1 except for using the sample solution 2 in place of the sample solution 1.

Composition 2: 4.0 M tetraethylammonium chloride, 0.1 M Tris

Comparative Example 1

An aqueous solution having a composition 3 described below was subjected to the same heat treatment and cooling treatment as described in Example 1 to thereby provide a sample solution 3. Then, the blockage current was measured and evaluated in the same manner as in Example 1 except for using the sample solution 3 in place of the sample solution 1.

Composition 3: 1.0 M potassium chloride, 0.1 M Tris

Comparative Example 2

An aqueous solution having a composition 4 described above was subjected to the same heat treatment and cooling treatment as described in Example 1 to thereby provide a sample solution 4. Then, the blockage current was measured and evaluated in the same manner as in Example 1 except for using the sample solution 4 in place of the sample solution 1.

Composition 4: 4.0 M ammonium chloride, 0.1 M Tris

Comparative Example 3

A sample solution 5 was provided in the same manner as in Example 1 except for not performing a heat treatment and cooling treatment. The blockage current was measured and evaluated in the same manner as in Example 1 except for using the sample solution 5 in place of the sample solution 1.

Comparative Example 4

A sample solution 6 was provided in the same manner as in Example 2 except for not performing a heat treatment and cooling treatment. The blockage current was measured and evaluated in the same manner as in Example 1 except for using the sample solution 6 in place of the sample solution 1.

Comparative Example 5

A sample solution 7 was provided in the same manner as in Example 3 except for not performing a heat treatment and cooling treatment. The blockage current was measured and evaluated in the same manner as in Example 1 except for using the sample solution 7 in place of the sample solution 1.

Comparative Example 6

A sample solution 8 was provided in the same manner as in Example 4 except for not performing a heat treatment and cooling treatment. The blockage current was measured and evaluated in the same manner as in Example 1 except for using the sample solution 8 in place of the sample solution 1.

The evaluation results of Examples 1 to 2 and Comparative Examples 1 to 6 are shown in Table 1.

TABLE 1

| | Sample solution | Cation species | Fusing step | clog | Number of events | Number of long term blockages | Frequency [%] |
|---|---|---|---|---|---|---|---|
| Example 1 | 1 | TMA+ | present | absent | 474 | 2 | 0.42 |
| Example 2 | 2 | TEA+ | present | absent | 1276 | 25 | 1.96 |
| Comparative Example 1 | 3 | K+ | present | present | — | — | — |
| Comparative Example 2 | 4 | NH4+ | present | present | — | — | — |
| Comparative Example 3 | 5 | TMA+ | absent | present | — | — | — |
| Comparative Example 4 | 6 | TEA+ | absent | present | — | — | — |
| Comparative Example 5 | 7 | K+ | absent | present | — | — | — |
| Comparative Example 6 | 8 | NH4+ | absent | present | — | — | — |

In Comparative Examples 1 to 6, although some DNA passing events were observed, clog of the nanopore occurred, whereas clog of the nanopore did not occur in Examples 1 to 2. The experimental results confirmed that when a sample solution that contains the cation (A) and that is provided through a fusing treatment is used, even in the case of analysis of a single strand DNA which is liable to undergo self-hybridization, clog of a nanopore can be suppressed to thereby achieve the analysis. The effect of suppressing clog of a nanopore is supposedly achieved in the following manner: a higher-order structure of the single strand DNA is fused, which allows the cation (A) (TMA+ or TEA+ in this Example) to approach the part where the higher-order structure is fused, and the cation (A) thus forms a physical steric hindrance to inhibit the formation of a complex higher-order structure by a hydrogen bond. Note that the supposition is not to limit the present invention.

In Examples 1 and 2, a heat treatment and a cooling treatment (rapid cooling) were performed as a means for fusing a higher-order structure, but the present invention is not to be limited thereto.

As described in the above embodiment, as a substance having a higher electrical conductivity than a quarternary alkyl ammonium chloride (specifically, tetramethylammonium chloride or tetraethylammonium chloride), potassium chloride, ammonium chloride, or the like can be used. The following experiment was performed in order to investigate whether the measurement without clog is possible and in addition, a high electrical conductivity can be obtained in the blockage current measurement also in the case where such a substance is used together with a quarternary alkyl ammonium chloride. In the experiment, the noise level was also evaluated since increased noise is not desirable even when the electrical conductivity is increased.

Example 3

An aqueous solution having a composition 5 described below was subjected to the same heat treatment and cooling treatment as described in Example 1 to thereby provide a sample solution 9. Then, the blockage current was measured and evaluated in the same manner as in Example 1 except for using the sample solution 9 in place of the sample solution 1.

Composition 5: 1.7 M potassium chloride, 1.5 M tetraethylammonium chloride, 0.1 M Tris

Example 4

An aqueous solution having a composition 6 described below was subjected to the same heat treatment and cooling treatment as described in Example 1 to thereby provide a sample solution 10. Then, the blockage current was measured and evaluated in the same manner as in Example 1 except for using the sample solution 10 in place of the sample solution 1.

Composition 6: 2.0 M ammonium chloride, 1.5 M tetraethylammonium chloride, 0.1 M Tris

Example 5

An aqueous solution having a composition 7 described below was subjected to the same heat treatment and cooling treatment as described in Example 1 to thereby provide a sample solution 11. Then, the blockage current was measured and evaluated in the same manner as in Example 1 except for using the sample solution 11 in place of the sample solution 1.

Composition 7: 2.0 M ammonium chloride, 1.5 M tetramethylammonium chloride, 0.1 M Tris The evaluation results of Examples 3 to 5 and, as a reference, that of Comparative Example 1 are shown in Table 2. The "noise" shows a value of the standard deviation after filtering at 2 kHz on the data obtained by the measurement.

TABLE 2

| | Sample solution | Salt containing cation | Electrode | Noise [pA] | clog | Number of events | Number of long term blockages | Frequency [%] |
|---|---|---|---|---|---|---|---|---|
| Comparative Example 1 | 3 | — | potassium chloride (1.0M) | 48.1 | present | — | — | — |
| Example 3 | 9 | tetraethylammonium chloride (1.5M) | potassium chloride (1.7M) | 35.5 | absent | 224 | 13 | 5.8 |
| Example 4 | 10 | tetraethylammonium chloride (1.5M) | ammonium chloride (2.0M) | 35.4 | absent | 482 | 12 | 2.9 |
| Example 5 | 11 | tetramethylammonium chloride (1.5M) | ammonium chloride (2.0M) | 31.0 | absent | 4020 | 7 | 0.2 |

Examples 3 to 5 shows that, by adding to the salt containing the cation (A) an electrolyte (potassium chloride or ammonium chloride in the Examples) having a higher electrical conductivity than the salt, the noise can be reduced while retaining the clog suppressing effect.

REFERENCE SIGNS LIST

101 Chamber unit
102 Nanopore
103 Substrate
103a Base (base material)
103b Thin layer
103c Insulating layer
104 Sample introducing area
105 Sample flow-out area
106 First flow-in channel
107 Second flow-in channel
108 First flow-out channel
109 Second flow-out channel
110 First liquid
111 Second liquid
113 Sample (biomolecule)
114 First electrode
115 Second electrode
117 Ammeter-equipped power source
201 Temperature controlling means

The invention claimed is:

1. A method for treating a biomolecule for an analysis using a nanopore, the method comprising:
   providing a sample solution containing an ammonium cation represented by a formula (1) shown below and a biomolecule with at least a part of a higher-order structure fused,
   wherein said providing the sample solution comprises steps of
   mixing at least the cation and the biomolecule to prepare a solution; and
   subjecting the solution containing the cation and the biomolecule to a heat treatment followed by cooling the solution at a rate of 10° C./second to 4° C. and maintaining the temperature of the solution at 4° C. for 5 minutes to fuse said at least a part of the higher-order structure of the biomolecule, and
   wherein said formula (1) is:

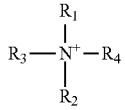

wherein $R_1$ to $R_4$ each independently represent a hydrogen atom or an organic group, provided that not all of $R_1$ to $R_4$ are hydrogen atoms.

2. The method according to claim 1, wherein the cation is a quarternary ammonium cation.

3. The method according to claim 1, wherein the cation is a quarternary alkyl ammonium cation.

4. The method according to claim 1, wherein the sample solution further comprises an electrolyte that has a higher electrical conductivity than a salt used for incorporating the cation into the sample solution.

5. The method according to claim 4, wherein the cation is a quarternary ammonium cation and the electrolyte is an ammonium salt.

6. The method according to claim 1, wherein the biomolecule is a nucleic acid.

7. The method according to claim 1, wherein the temperature of the solution before cooling is in the range of 90° C. to 100° C.

8. The method according to claim 7, wherein the temperature of the solution before cooling is held at 95° C. for 15 minutes.

* * * * *